United States Patent
Hamidi

(10) Patent No.: US 9,370,488 B2
(45) Date of Patent: Jun. 21, 2016

(54) METHOD AND SYSTEM FOR SYNTHESIZING NANOCARRIER BASED LONG ACTING DRUG DELIVERY SYSTEM FOR INSULIN

(71) Applicant: Mehrdad Hamidi, Tehran (IR)

(72) Inventor: Mehrdad Hamidi, Tehran (IR)

(73) Assignees: Kimia Zist Parsian (KZ); Tehram (IR)

(*) Notice: Subject to any disclaimer, the term of this patent is extended or adjusted under 35 U.S.C. 154(b) by 47 days.

(21) Appl. No.: 14/337,072

(22) Filed: Jul. 21, 2014

(65) Prior Publication Data
US 2015/0017229 A1    Jan. 15, 2015

(51) Int. Cl.
| A61K 9/51 | (2006.01) |
| A61K 9/127 | (2006.01) |
| A61K 38/28 | (2006.01) |
| A61K 9/00 | (2006.01) |

(52) U.S. Cl.
CPC .............. *A61K 9/127* (2013.01); *A61K 9/0019* (2013.01); *A61K 9/1277* (2013.01); *A61K 9/5123* (2013.01); *A61K 9/5138* (2013.01); *A61K 9/5146* (2013.01); *A61K 9/5161* (2013.01); *A61K 9/5192* (2013.01); *A61K 38/28* (2013.01); *Y10S 977/773* (2013.01); *Y10S 977/906* (2013.01); *Y10S 977/907* (2013.01)

(58) Field of Classification Search
None
See application file for complete search history.

(56) References Cited

U.S. PATENT DOCUMENTS

| 9,186,326 B2* | 11/2015 | Hamidi | A61K 9/1277 |
| 2006/0252839 A1* | 11/2006 | Roberts et al. | 514/712 |
| 2009/0285882 A1* | 11/2009 | Weiss et al. | 424/450 |

OTHER PUBLICATIONS

JN Israelachvili, S Marcelja, RG Horn. "Physical Principles of Membrane Organization." Quarterly Reviews of Biophysics, vol. 13 No. 2, 1980, pp. 121-200.*
RH Muller, K Mader, S Gohla. "Solid lipid nanoparticles (SLN) for controlled drug delivery—a review of the state of the art." European Journal of Pharmaceutics and Biopharmaceutics, vol. 50, 2000, pp. 161-177.*
H Takeuchi, H Yamamoto, T Niwa, T Hino, Y Kawashima. "Enteral Absorption of Insulin in Rats from Mucoadhesive Chitosan-Coated Liposomes." Pharmaceutical Research, vol. 13 No. 6, 1996, pp. 896-901.*
Z-H Wu, Q-N Ping, Y Wei, J-M Lai. "Hypoglycemic efficacy of chitosan-coated insulin liposomes after oral administration in mice." Acta Pharmacologica Sinica, vol. 25 No. 7, Jul. 2004, pp. 966-972.*

(Continued)

*Primary Examiner* — Isaac Shomer
(74) *Attorney, Agent, or Firm* — Barry Choobin; Patent 360

(57) ABSTRACT

The embodiments herein provide a long-acting injectable drug (insulin) delivery nano-carrier system and a method of synthesizing the same. The insulin entrapped nanoparticles are prepared using a lipid/phospholipid core which is coated by a polymer. The lipid and phospholipid are dissolved in organic solvent. This solution is transferred into an aqueous phase consisting of distilled water or a buffer and dissolved insulin. A solution of polymer is added drop wise. The drug entrapped nanoparticle formation is achieved by diffusion of the organic solvent within the aqueous solvent to obtain the nanoparticles. The drug gets entrapped within the formed nanoparticles via the anti-solvency effect of the aqueous matrix. The resulting drug nanocarriers are capable of releasing the drug in a slow rate upon injection. The synthesized drug carrying nanoparticles are cryopreserved stored for future administration. For better storage the nanodispersion is dried to form a powder.

8 Claims, 7 Drawing Sheets

(56) References Cited

OTHER PUBLICATIONS

P Fonte, F Andrade, F Araujo, C Andrade, J das Neves, B Sarmento. "Chapter Fifteen: Chitosan-Coated Solid Lipid Nanoparticles for Insulin Delivery." Methods in Enzymology, vol. 508, 2012, pp. 295-314.*

ELS Carvalho, A Grenha, C Remunan-Lopez, MJ Alonso, B Seijo. "Mucosal Delivery of Liposome-Chitosan Nanoparticle Complexes." Methods in Enzymology, vol. 465, 2009, pp. 289-312.*

* cited by examiner

METHOD AND SYSTEM FOR SYNTHESIZING NANOCARRIER BASED LONG ACTING DRUG DELIVERY SYSTEM FOR INSULIN

BACKGROUND

1. Technical Field

The embodiments herein generally relate to the field of molecular nanotechnology. The embodiments herein particularly relate to nanomedicines or nanocarrier based drug delivery systems. The embodiments herein more particularly relate to a system and method for synthesizing long acting, and slow release nanoparticle or nano carrier based drug delivery system for Insulin.

2. Description of the Related Art

In nanotechnology, a particle is defined as a small object that becomes a whole unit with respect to its transport and properties. The particles are further classified according to the diameter. The "nanoparticles" have a diameter within a range of 1 and 100 nanometer.

Nanotechnology has offered many advantages for novel drug delivery systems in terms of both time-controlled drug delivery and site-directed drug delivery. These advantages are mainly derived from the very small (submicron) sizes of the nanostructures used as nanocarriers for drugs as well as the possibility of engineering the carrier structure and/or surface according to the particular biological requirements.

"Nanomedicine" is the medical application of nanotechnology. Nanomedicine ranges from the medical applications of nonmaterial's to nano-electronic biosensor and even possible future applications of molecular nanotechnology.

The current problems for nano-medicine involve understanding the issues related to toxicity and the environmental impact on a nanoscale material.

The nano-medicine has provided the possibility of delivering drugs to specific cells using nanoparticles. The overall drug consumption and side effects are lowered significantly by depositing an active agent only in a morbid region at a required and appropriate dosage thereby eliminating a need for a higher dosage.

Drug delivery researchers are developing nanoscale particles or molecules to improve a "bioavailability" of a drug. The term bioavailability refers to the presence of drug molecules where they are used in the body and where they act against an ailment. Drug delivery system mainly focuses on maximizing the bioavailability both at specific places in the body and over a period of time.

The drug delivery systems such as lipid or polymer based nanoparticles are designed to improve the pharmacological and therapeutic properties of the drugs. Further, the metal based nanoparticles are also designed and developed to deliver the drugs.

The commonly used metals for nano-drug delivery system include but not limited to gold, silver, platinum etc. The metal based nanoparticles for the drug delivery system show toxicity. The recent studies in this arena have shown that positively charged gold nanoparticles are found to enter kidney, while negatively charged gold nanoparticles remained in the liver and spleen. The positive surface charges of the nanoparticles decreases the rate of opsonization of nanoparticles in the liver, thereby affecting the excretory pathway. Even a relatively small size of the nanoparticles such as 5 nm can become compartmentalized in the perinephral tissues, and accumulate in the body over tissues. The advancement of research proves that targeting and distribution can be augmented by nanoparticles and the dangers of nano-toxicity have become an important question for the medical use in drug delivery.

A drug may cause tissue damage, but a drug delivery with regulated drug release can eliminate the problem. When a drug is removed too quickly from the body, this rapid drug delivery could force a patient to use a dose higher than a necessary dose. But a clearance can be reduced with drug delivery systems by altering the pharmacokinetics of the drug. A poor bio-distribution is a problem that can affect normal tissues through a widespread drug distribution, but the particulates from the drug delivery systems lower the volume of distribution and release the effect on a non-target tissue. The potential nano-drugs works by very specific and well understood mechanisms, one of the major impacts of nanotechnology and nano-science is the development of completely new drug delivery systems with more useful behaviors and less side effects.

Long-acting injectable drug delivery systems can benefit from the potentials of nanotechnology via the slow drug release from the nano-carriers already being loaded by the drug of interest. These drug carriers may be administered by injection into the host body through different routes mainly including intravenous, intramuscular, subcutaneous, intradermal, intra-arterial, intra-thechal, and intra-cardiac administration. Basically, a drug dose loaded in a nano-carrier is administered and the carrier, then supplies the drug needed for the particular pharmacological effect for a more extended time following a single dose compared to a conventional bolus dose. The pharmacokinetic outcome of the injectable long-acting dosage form is expected to be the lack of fluctuations in plasma concentrations of the drug which, eventually, results in avoiding the risks of over dosages, i.e., toxicity, or under dosages, i.e., treatment failure, in drug therapy. When a particular drug is administered in a chronic (long-term) basis in the form of repeated doses, a fluctuation in drug concentrations in plasma is observed. These pharmacokinetic fluctuations directly result in pharmacodynamic fluctuations where the drug affects the site of action and experiences peaks and troughs at the same time of concentration changes or after a lag phase. These fluctuations in the drug concentration are highly risky for patient, in particular for a drug like methadone with narrow therapeutic index (small differences between therapeutic and toxic doses). With the conventional, currently available products of the drug in the market, there is always a risk for the patient to experience an overdosage (toxic effects in brain or other tissues) in the peak times or an underdosage (insufficient drug effect), both the stages are harmful for the patient.

Diabetes mellitus (DM) is also known as simply diabetes, is a group of metabolic diseases in which high blood sugar levels are present over a prolonged period. The high blood sugar produces the symptoms of frequent urination, increased thirst and increased hunger. The acute complications include diabetic ketoacidosis, and ketotic hyper-osmolar coma. Serious long-term complications of diabetes include heart diseases, stroke, kidney failure, foot ulcer and damage to the eyes. Diabetes is caused when the pancreas does not produce enough insulin, or the cells of the body do not respond properly to the insulin produced. There are 3 types of diabetes mellitus. They are known as Type 1 Diabetes mellitus (DM); Type 2 Diabetes mellitus (DM) and Gestational Diabetes.

Type 1 Diabetes mellitus (DM)—occurs, when the body of a person fails to produce enough insulin. This form is referred to as "insulin dependent diabetes mellitus" (IDDM) or "juvenile diabetes". Type 2 Diabetes mellitus (DM) begins with insulin resistance, a condition in which cells fail to respond to insulin properly. As the disease progresses a lack of insulin may also develop. This is referred to as non-insulin dependent diabetes mellitus (NIDDM). Gestational diabetes is the third main form of diabetes. It occurs when pregnant women without a previous history of diabetes develop a high blood glucose level.

The diabetes is managed by diet regime, medications (such as metformin), pancreatic transplantation and stem cell therapy to restore pancreatic function. Type 1 diabetes is typically treated with a combination of regular NPH insulin or synthetic insulin analogs. Insulin used in type 2 diabetes, a long acting formulation is usually added initially while continuing oral medications.

The major problem for the patients requiring external insulin is the right dose of insulin and the right timing of administration. The symptoms of low blood sugar levels that are brought on by an insulin overdose include anxiety, confusion, extreme hunger, fatigue, irritability, sweating or clammy skin, trembling hands. The prolonged use of insulin overdose may lead to protein accumulation in kidney resulting in renal failure.

The formulation of a long-acting product form of insulin has a potential to improve the condition of diabetic patient. The potential of insulin nanocarrier is testified by the long acting nature, slow and controlled release of the insulin from the nanocarrier. The lipid based as well as polymeric-based nanoparticles are prepared and loaded with the drug insulin which upon entry to the host body via injection serves as a drug reservoir. The insulin reservoir is capable of releasing the insulin drug for long time periods in blood circulation. This long-term drug profile is used as a basis for prolonged chronic drug action toward the desired effects against diabetes. The fluctuations in the drug like insulin have negative impact on the blood glucose levels.

Hence there is a need to develop a nanoparticle based drug delivery system for insulin without any threat of cytotoxicity. Also there is a need for a nanoparticle drug delivery system for insulin to release the drug slowly and in a controlled manner to an action site. Further there is a need to develop a method for synthesizing the organic biomolecule based nanoparticle drug delivery system for insulin.

The above mentioned shortcomings, disadvantages and problems are addressed herein and which will be understood by reading and studying the following specification.

OBJECTIVES OF THE EMBODIMENTS

The primary objective of the embodiments herein is to synthesize a nano carrier based long acting drug delivery system for insulin using an aqueous core with lipid core coated with a polymer.

Another objective of the embodiments herein is to synthesize the drug carrying nanoparticles or nanocarrier entrapping insulin within the nanoparticles.

Yet another objective of the embodiments herein is to synthesize the drug nanocarrier based long acting drug delivery system for insulin to provide a controlled release of the drug at a slow rate upon administration to an individual.

Yet another objective of the embodiments herein is to synthesize the drug nanocarrier based long acting drug delivery system for insulin to enable an administration of a drug through intravenous, intramuscular, subcutaneous, intra-dermal, intra-arterial, intra-thecal and intra-cardiac routes.

Yet another objective of the embodiments herein is to synthesize the drug nanocarrier based long acting drug delivery system for insulin by entrapping the drug using the anti-solvency effect of the aqueous matrix.

Yet another objective of the embodiment herein is to synthesize the drug nanocarrier based long acting drug delivery system for insulin to cryoprotect the drug nanocarrier for future use and application.

These and other objects and advantages of the embodiments herein will become readily apparent from the following detailed description taken in conjunction with the accompanying drawings.

SUMMARY

The various embodiments herein provide a method and system for the synthesis of the nanocarrier based drug delivery system for insulin. The drug carrying nanoparticles or nanocarriers are prepared using a lipid/phospholipid core coated with a polymer. The nanocarriers entrap the insulin drug for site directed drug delivery and slow release.

Insulin is a pepetide hormone, produced by beta cells in the pancreas. Insulin plays a major role in regulating the carbohydrate and fat metabolism in the body. The insulin helps the skeletal muscle cells and fat tissues to absorb glucose from the blood. The human insulin protein is composed of 51 amino acids. The molecular weight of insulin is 5808 Dalton. Insulin is a dimer of an A-chain and a B-chain. The A chain and B chain are linked together by disulfide bonds. Chain A has 21 amino acids and chain B has 30 amino acids.

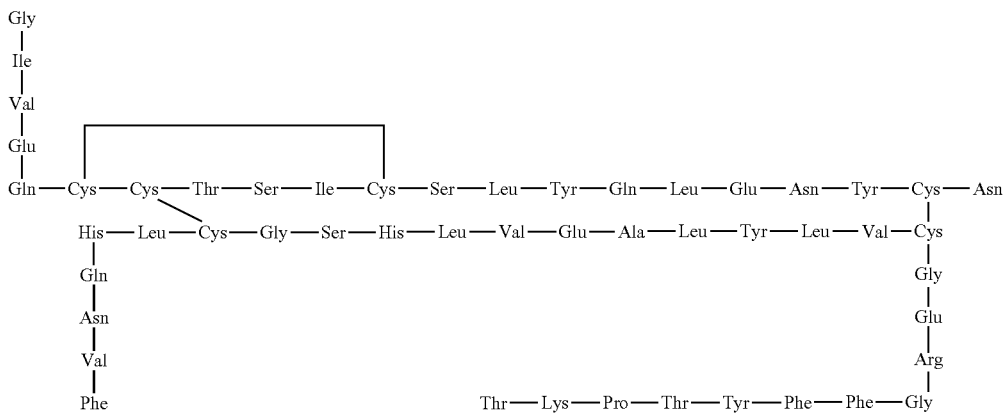

According to one embodiment herein, a system and a method is provided for synthesizing slow and controlled release of an insulin entrapped in a nanoparticle or nanocarrier. According to one embodiment herein, the method comprises the steps of dissolving the insulin in water or buffer solution to get an aqueous phase. The insulin is dissolved at a concentration of 0.1 to 10 mg/ml in the organic solvent. The organic solvent is 0.1 to 5 mg/ml. A phospholipid is added to the organic solution to form a bilayer around the insulin. A lipid is also added to the organic solution to obtain an organic solution mixture. Further, the lipid forms a layer around the aqueous mixture comprising insulin. The organic solution mixture comprises organic solvent with phospholipid and lipid. The organic solution mixture is added in drops or dropwise to an aqueous solution to form a lipid core around the aqueous solution. The aqueous solution has a pH in a range of 3-11. A volume ratio of the organic solution mixture to the aqueous solution is within 0.05 to 3. A buffered solution of a polymer is added to the aqueous solution with lipid core to form a coating layer around the lipid core to obtain a nano carrier. The pH of the polymer solution is in a range of 3.5 to 11. The polymer solution is added dropwise or in drops to the aqueous solution in a volume ratio of 0.05 to 1.

The organic solvent is selected from a group consisting of a methanol, an ethanol, an acetone and an isopropanol. The phospholipid is selected from a group consisting of a phosphatidylcholine, a phosphatidylethanolamine, a phosphatidylinositol. The lipid is selected from a group consisting of a monostearyl glycerol, a distearyl glycerol, a palmitic acid, a stearic acid and a glyceryl stearate. The polymer is selected from a group consisting of a chitosan, a polyethylene glycol, a polyvinyl alcohol.

According to one embodiment herein, a system is provided for a slow and controlled release of an insulin entrapped in nanoparticle or nanocarrier. The system comprises a core of aqueous phase or solution with the insulin, a lipid layer, a phospholipid bilayer and a polymer coating. The aqueous solution is made of water or a buffer. The phospholipid is selected from a group consisting of a phosphatidylcholine, a phosphatidylethanolamine, a phosphatidylinositol. The lipid is selected from a group consisting of a monostearyl glycerol, a distearyl glycerol, a palmitic acid, a stearic acid and a glyceryl stearate. The polymer is selected from a group consisting of a chitosan, a polyethylene glycol, a polyvinyl alcohol.

The insulin is water-soluble and presents in an aqueous solution during a formation of a nanovesicle. The insulin gets loaded to the nanocarriers in a dissolved state within the aqueous solution. The insulin nanocarrier or nanoparticle particle size distribution curve exhibit a peak of 128.5 nm, and wherein insulin nanocarrier has a relative low polydisparity index of 0.180. The insulin nanocarrier or nanoparticle has a zeta potential within a range of 10 mv to 30 mv. The insulin nanocarrier or nanoparticle has a zeta deviation of 4.71 mv. The insulin nanocarriers or nanoparticles are administered intravenously, intramuscularly, sub-cutaneously, intra-dermally, intra-arterially, intra-thecaly and intra-cardiac routes.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The other objects, features and advantages will occur to those skilled in the art from the following description of the preferred embodiment and the accompanying drawings in which.

Figure 1:
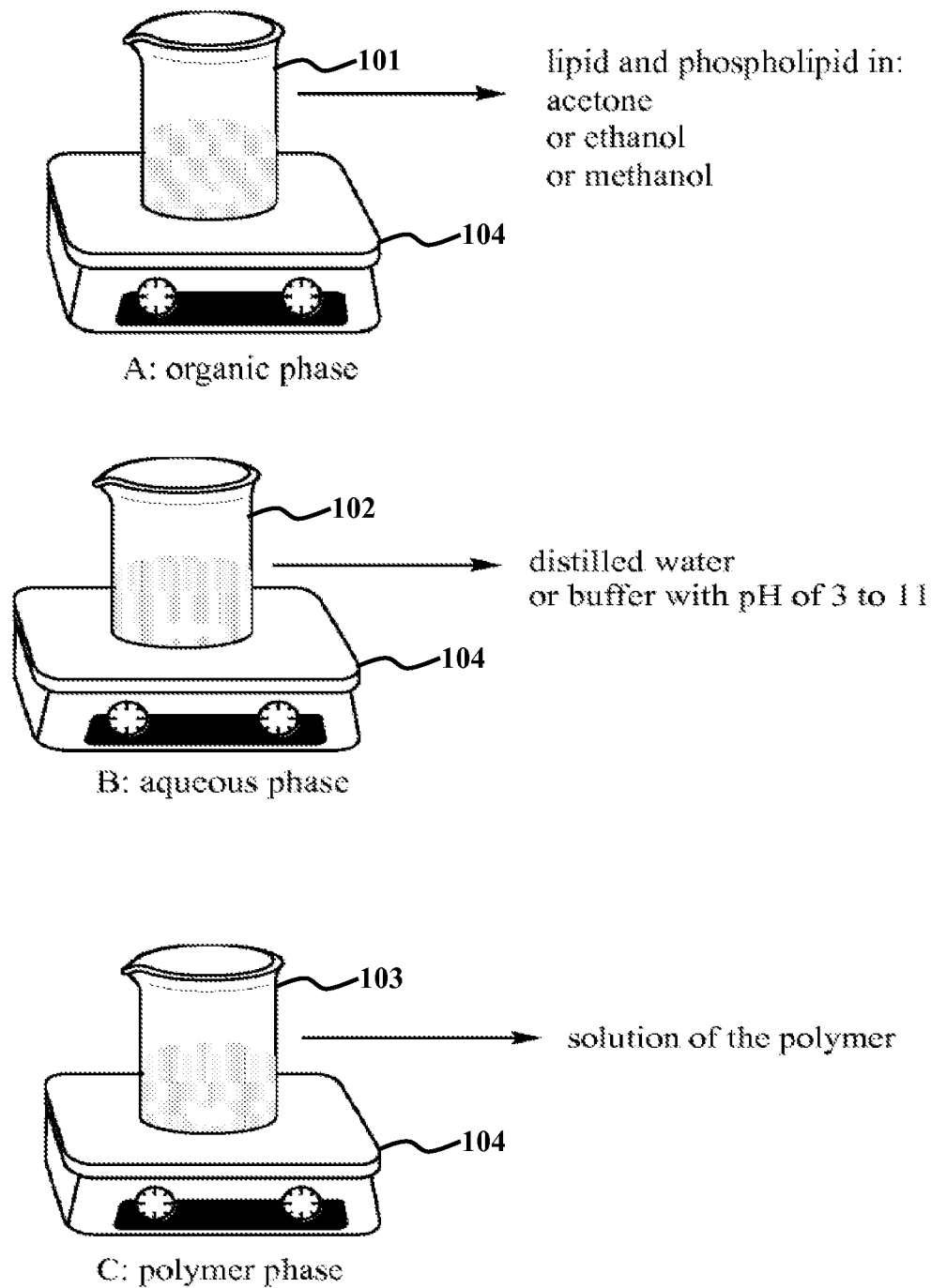
FIG. 1 illustrates a schematic representation of the processes for the preparation of organic phase, aqueous phase and polymer phase solutions in the method for synthesizing a nano carrier based long acting drug delivery system for insulin, according to an embodiment herein.

Although the specific features of the embodiments herein are shown in some drawings and not in others. This is done for convenience only as each feature may be combined with any or all of the other features in accordance with the embodiments herein.

DETAILED DESCRIPTION OF THE EMBODIMENTS

In the following detailed description, a reference is made to the accompanying drawings that form a part hereof, and in which the specific embodiments that may be practiced is shown by way of illustration. The embodiments are described in sufficient detail to enable those skilled in the art to practice the embodiments and it is to be understood that the logical, mechanical and other changes may be made without departing from the scope of the embodiments. The following detailed description is therefore not to be taken in a limiting sense.

The various embodiments herein provide a method and system for the synthesis of the nanocarrier based drug delivery system for insulin. The drug carrying nanoparticles or nanocarriers are prepared using a lipid/phospholipid core coated with a polymer. The nanocarriers entrap the insulin drug for site directed drug delivery and slow release.

Insulin is a peptide hormone, produced by beta cells in the pancreas and plays a major role in regulating carbohydrate and fat metabolism in the body. The insulin helps the skeletal muscle cells, fat tissues to absorb glucose from the blood. The human insulin protein is composed of 51 amino acids, and has a molecular weight of 5808 Dalton. It's a dimer of an A-chain and a B-chain. The A chain and B chain are linked together by the disulfide bonds. The chain A has 21 amino acids and chain B has 30 amino acids.

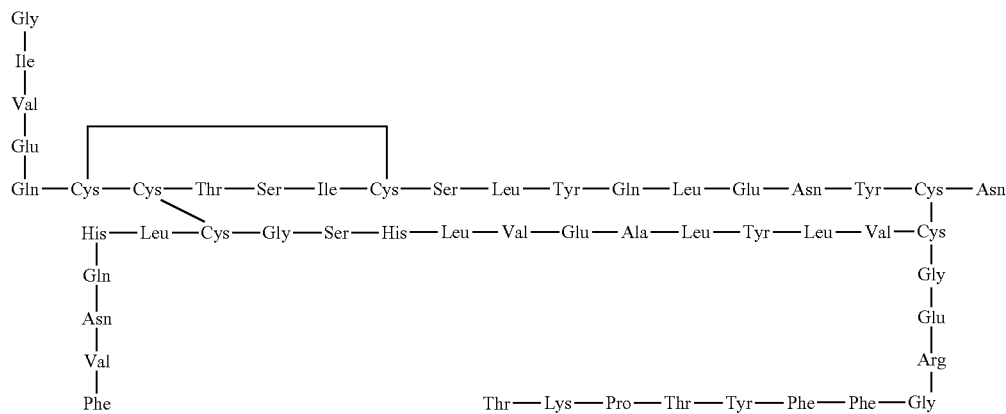

According to one embodiment herein, a method is provided for synthesizing slow and controlled release of an insulin entrapped in a nanoparticle or nanocarrier. The method comprises the steps of dissolving the insulin in a water or a buffer solution to get an aqueous phase. The insulin is dissolved at a concentration of 0.1 to 10 mg/ml in the organic solvent. The organic solvent is taken in a concentration of 0.1 to 5 mg/ml. A phospholipid is added to the organic solution. A lipid is also added to the organic solution to obtain an organic solution mixture. Further the lipid forms a layer around the aqueous mixture comprising insulin. The organic solution mixture comprises organic solvent with phospholipid and lipid. The organic solution mixture is added in drops or dropwise to an aqueous solution comprising dissolved insulin to form a lipid core around the aqueous solution. The aqueous solution has a pH in a range of 3-11. A volume ratio of the organic solution mixture to the aqueous solution is within 0.05 to 3. A buffered solution of a polymer is added to the aqueous solution with lipid core to form a coating layer around the lipid core and to obtain the insulin nano carrier. The pH of the polymer solution is in a range of 3.5 to 11. The polymer solution is added dropwise or in drops to the aqueous solution in a volume ratio of 0.05 to 1.

The organic solvent is selected from a group consisting of a methanol, an ethanol, an acetone and an isopropanol. The phospholipid is selected from a group consisting of a phosphatidylcholine, a phosphatidylethanolamine, a phosphatidylinositol. The lipid is selected from a group consisting of a monostearyl glycerol, a distearyl glycerol, a palmitic acid, a stearic acid and a glyceryl stearate. The polymer is selected from a group consisting of a chitosan, a polyethylene glycol, a polyvinyl alcohol.

According to one embodiment herein, a system is provided for a slow and controlled release of an insulin entrapped in a nanoparticle or nanocarrier. The system comprises a core of aqueous phase or solution with the insulin, a lipid layer, a phospholipid bilayer and a polymer coating. The aqueous solution is made of water or a buffer. The phospholipid is selected from a group consisting of a phosphatidylcholine, a phosphatidylethanolamine, a phosphatidylinositol. The lipid is selected from a group consisting of a monostearyl glycerol, a distearyl glycerol, a palmitic acid, a stearic acid and a glyceryl stearate. The polymer is selected from a group consisting of a chitosan, a polyethylene glycol, a polyvinyl alcohol.

The insulin is water-soluble protein and presents in an aqueous solution during a formation of a nanovesicle. The insulin gets loaded to the nanocarriers in a dissolved state in the aqueous solution. The insulin nanocarrier or nanoparticle particle size distribution curve exhibit a peak of 128.5 nm, and wherein insulin nanocarrier has a relative low polydisparity index of 0.180. The insulin nanocarrier or nanoparticle has a zeta potential within a range of 10 mv to 30 mv. The insulin nanocarrier or nanoparticle has a zeta deviation of 4.71 mv. The insulin nanocarriers or nanoparticles are administered intravenously, intramuscularly, sub-cutaneously, intra-dermally, intra-arterially, intra-thecaly and intra-cardiac routes.

According to an embodiment herein, the drug carrying nanoparticles are prepared using a lipid/phospholipid core, which is then, coated by a polymer. The lipid part comprises of stearic acid, lipoic acid, monostearin, distearin, and cholesterol are used in conjugation with phospholipid part which acts as the stabilizer for the solid lipid. The phosphatidyl choline (lecithin) and/or phosphatidyl ethanolamaine are used as the phoospholipid part. The chitosan, alginate, poly (vinyl alcohol), poly (ethylene glycol), poly (vinyl pyrrolidone) are the polymers used in this process for coating.

According to one embodiment herein, the first step in the process of synthesizing the insulin drug based nanocarriers is dissolving the lipid and phospholipid in an organic solvent. The organic solvent is chosen from a group comprising acetone, ethanol, and methanol. The concentration of the organic solvent is in the range of 0.1 to 5 mg/ml. The solution of lipid and phospholipid in an organic solvent is transferred into an aqueous phase consisting of distilled water or a buffer with pH of 3-11. The drug (insulin) to be entrapped in the nanoparticles/nanocarriers is present in the aqueous phase at a concentration of 0.1 to 10 mg/ml. The volume ratio of organic-to-aqueous phase solution mixture is within a range of 0.05-3. The solution mixture obtained is mixed with a solution of the polymer. The polymer solution is prepared in a buffered medium with a pH range of 3.5 to 11.0. The polymer solution is added drop-wise to the organic-to-aqueous phase mixture in a volume ratio of 0.05 to 1.

According to an embodiment herein, the nanocarriers are capable of releasing the insulin drug in a slow rate upon injection via intravenous, intramuscular, subcutaneous, intradermal, intrathecal and intracardiac routes.

According to one embodiment herein, the particle formation is achieved mechanistically by the diffusion (dilution) of the organic solvent within the aqueous host solvent to obtain the nano particles. The drug of interest such as insulin is entrapped in the nanoparticles/nanocarrier via the antisolvency effect of the aqueous matrix. The basis for the preparation of the phospholipid-based nanocarriers is a method known as "ethanol injection" with some modifications. In this method, the phospholipid which is practically insoluble in water, is dissolved in a water-miscible solvent, typically ethanol. The ethanol is gradually added drop-wise to a higher amount of water (for example 10-times the ethanolic solution volume). When the phospholipid comes into contact with ethanol in the water phase, ethanol "diffuses" into the water phase and becomes diluted leading to formation of new solvent which is mainly water with a small portion of the ethanol. Since the phospholipid cannot be dissolved in this new solvent and there is a vigorous shaking in system on the other hand, the amphiphilic phospholipids undergoes self-assemble process by using the vesicles made of phospholipid bilayers as their shells and an entrapped water phase as the core and the core is surrounded by the phospholipid bilayers. The drug such as "insulin", which is soluble in water or a buffer, presents itself in the aqueous medium at the time of nanovesicle formation. Thermodynamically the lipid and the phospholipid form a layer around the aqueous solution. As the drug (insulin) is hydrophilic, during the formation of the lipid and phospholipid self assemblies the insulin cannot be found in any proportion within the lipid core or phospholipid bilayer.

According to one embodiment herein, the nanocarrier has a lipid-phospholipid-polymer structure each of the components offer a definite property to the drug delivery system. The lipid fraction makes the system a suitable carrier for lipophilic drugs also. The lipid fraction restricts the rapid release of the drug from the nanocarrier. The phospholipid component makes the system more amphiphillic to incorporate the lipophillic, the hydrophilic and the amphiphillic drugs. The presence of this phospholipid fraction offers the self assembly behavior to the nanocarrier. The polymer forming a coating on the outer shell of the nanocarrier provides a surface charge, fluidity and mechanical strength.

According to one embodiment herein, the materials used for the synthesis of the drug nanocarriers/nanoparticles are divided into four groups. The four groups are organic solvents, phospholipids, lipids and polymers. The organic solvents which are used for the synthesis of the drug nanocarrier/nanoparticle are methanol, ethanol, acetone and isopropanol. The phospholipids which are used for the synthesis of the drug nanocarrier/nanoparticle are phosphatidylcholine, phosphatidylethanolamine and phosphatidylinositol. The lipids which are used for the synthesis of the drug nanocarrier/nanoparticle are monostearyl glycerol, distearyl glycerol, palmitic acid and stearic acid. The polymers which are used for the synthesis of the drug nanocarrier/nanoparticle are chitosan, polyethylene glycol, ad polyvinyl alcohol. The aqueous solution is a water or a buffer, which is used for the formation of the core.

According to one embodiment herein, the drug such as insulin in different concentrations is taken for the preparation of the drug carrying nanoparticles/nanocarriers based on specific objectives, therapeutic dosages and indications. The drug such as insulin is then dissolved in water or a buffer to get an aqueous solution. The lipid and the phospholipid are dissolved in organic solvent such as ethanol, methanol, or acetone to get a solution. The lipid (mainly a glyceryl stearate) is added in different amounts (quantities) to the organic solvent. The lipid is added in a specific concentration depending on the drug and organic solvent concentrations. This solution mixture consisting of organic solvent, phospholipid and lipid is added drop wise into an aqueous phase (water or buffer with insulin) to form the lipid cores. The buffered aqueous solution of the polymer with different concentrations is added dropwise onto the cores based on the amounts or quantities of other compounds present in the solution to form the coatings or shells around the phospholipid core.

According to one embodiment herein, the nanoparticle/nanocarriers are subjected to in-vitro characterization tests, after the synthesis of insulin drug entrapped nanoparticle/nanocarriers.

According to one embodiment herein, the particle size distribution of the nano-dispersion is evaluated using the Dynamic Light Scattering (DLS) method. The surface zeta potential of the nano-dispersion is also evaluated by the electrophoretic mobility method. The drug release profile of the nanoparticles is most important factor and is analyzed in vitro.

According to one embodiment herein, the synthesized drug loaded nanoparticle/nanocarrier is dried to form a powder using a freezer-dryer. The freeze-drying process enables the better storage. Glucose, lactose, trehalose, sorbitol, glycerol, mannitol or Tween are used in a concentration of 0.25-5%, for cryopreservation. The characterization reveals an aqueous core with drug (insulin) surrounded by a phospholipid bilayer. The lipid core is surrounded by the polymer shell. Two kinds of substances such as cryoprotectant and lyoprotectant are used for the cryopreservation by freeze-drying method of the drug loaded nanocarriers or nanoparticles. The role of cryoprotectant is to prevent irreversible aggregation of the nanoparticles during the freezing process. The cryoprotectant and lyoprotectant materials are mixed with the nanoparticles/nanocarriers (nano-dispersion) before drying. When the freezing process is carried out on the samples, the cryoprotectant and lyoprotectant materials provide either a physical barrier or an electrical barrier around each nanocarrier or align the particles in solid-liquid interfaces during the freezing process resulting in the protection of each individual carrier from being aggregated with the neighbouring particles. The lyoprotectants also play a similar role. The commonly used cryoprotectants and lyoprotectants are monosaccharides, disaccharides, polyols and non-ionic surfactants.

According to one embodiment herein, there are four mechanisms responsible for the drug release from a nanocarrier when administered to an individual. The mechanisms are passive diffusion, based on the Fickian kinetics, nanocarrier erosion occurring with time resulting in drug release, water penetration inside nanoparticles followed by channelling (the drug is dissolved and diffused based on the drug concentration gradient) and nanocarrier capture by the natural defence cells of the host body, then drug release out of the vehicle. These mechanisms contribute to the drug release from the nanocarrier.

FIG. 1 illustrates a schematic representation of the processes for the preparation of organic phase, aqueous phase and polymer phase solutions in the method for synthesizing a nano carrier based long acting drug delivery system for insulin, according to an embodiment herein. A lipid and a phospholipid are dissolved in an organic solvent in a beaker. The organic solvent are selected from an acetone or an ethanol or a methanol (101). The lipid and phospholipid are dissolved in the organic solvent by a magnetic stirrer 104. The lipid and phospholipid are dissolved in organic solvent such as ethanol, methanol, or acetone to get a solution (101). The lipid (mainly a glyceryl stearate) is added in different amounts (quantities) to the solution of methadone and organic solvent. The lipid is added in a specific concentration depending on the drug and organic solvent concentrations. This solution mixture consisting of organic solvent and lipid is added drop wise into an aqueous phase (water or buffer) with a drug (insulin) to form the lipid cores (102). The buffered aqueous solution of the polymer with different concentrations is added dropwise onto the cores based on the amounts or quantities of other compounds present in the solution to form the coatings or shells around the phospholipid core. Finally, a buffered aqueous solution of the polymer such as a poly cation with a pH of 3.5 to 11 and a concentrations based on the amount of other compounds is added dropwise onto the lipid cores to form the coats or layers around the lipid cores (103) and the drug entrapped nanocarrier is obtained. The polymer solution is added dropwise to the organic to aqueous phase in a volume ratio of 0.05 to 1. The insulin is water soluble and presents itself in the aqueous solution core which is entrapped by the lipid and phospholipid bilayer. In a beaker a lipid and a phospholipid are dissolved in an organic solvent. The organic solvent is selected from an acetone or an ethanol or a methanol. The lipid and phospholipid are dissolved in the organic solvent by a magnetic stirrer.

Figure 2:
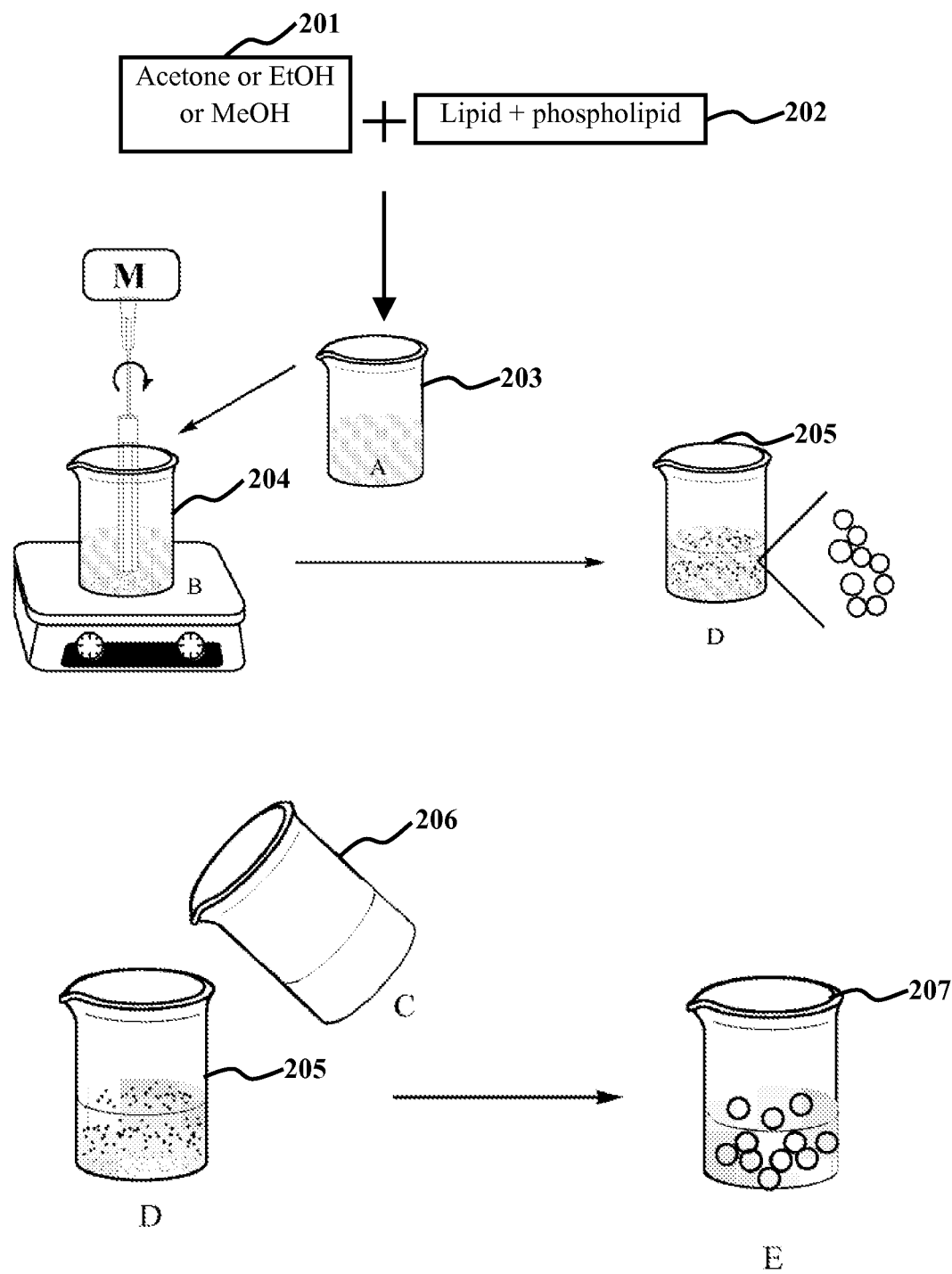
FIG. 2 illustrates a schematic representation of a method for synthesizing a nano carrier based long acting drug delivery system for insulin, according to an embodiment herein.

FIG. 2 illustrates a schematic representation of a method for synthesizing a nano carrier based long acting drug delivery system for insulin, according to an embodiment herein. The lipid and phospholipid, are dissolved in an organic solvent such as ethanol, methanol or acetone (201). The organic solvent has a concentration of 0.1 to 5 mg/ml. Then different amounts of the phospholipid, mainly phosphatidylcholine, are dissolved in this solution and, finally, the lipid, mainly a glyceryl stearate, is dissolved in the same solution with a preset concentration depending on the drug and the organic solvent components (202). The mixing of organic solvent with lipid and phospholipid yields a solution mixture-A (203). The insulin in different concentrations is taken based on the specific objectives, therapeutic dosages and indications. The insulin is dissolved in an aqueous phase. The solution-A is added dropwise onto the aqueous phase such as water or buffer with a pH in the range of 3-11 (204). The insulin to be entrapped is taken in the concentration of 0.1 to 10 mg/ml. The lipid cores-D are formed aqueous phase (205). The volume ratio of the organic to the aqueous phase mixtures is 0.05 to 3. Finally, a buffered aqueous solution of the polymer such as a poly cation with a pH of 3.5 to 11 with different concentrations, based on the amount of other compounds, is added dropwise onto the lipid cores to form the coats around the lipid cores (206) and the drug nanocarriers E are obtained (207). The polymer solution is added dropwise to the organic to aqueous phase in a volume ratio of 0.05 to 1. The insulin is water soluble and presents itself in the aqueous core.

Figure 3:
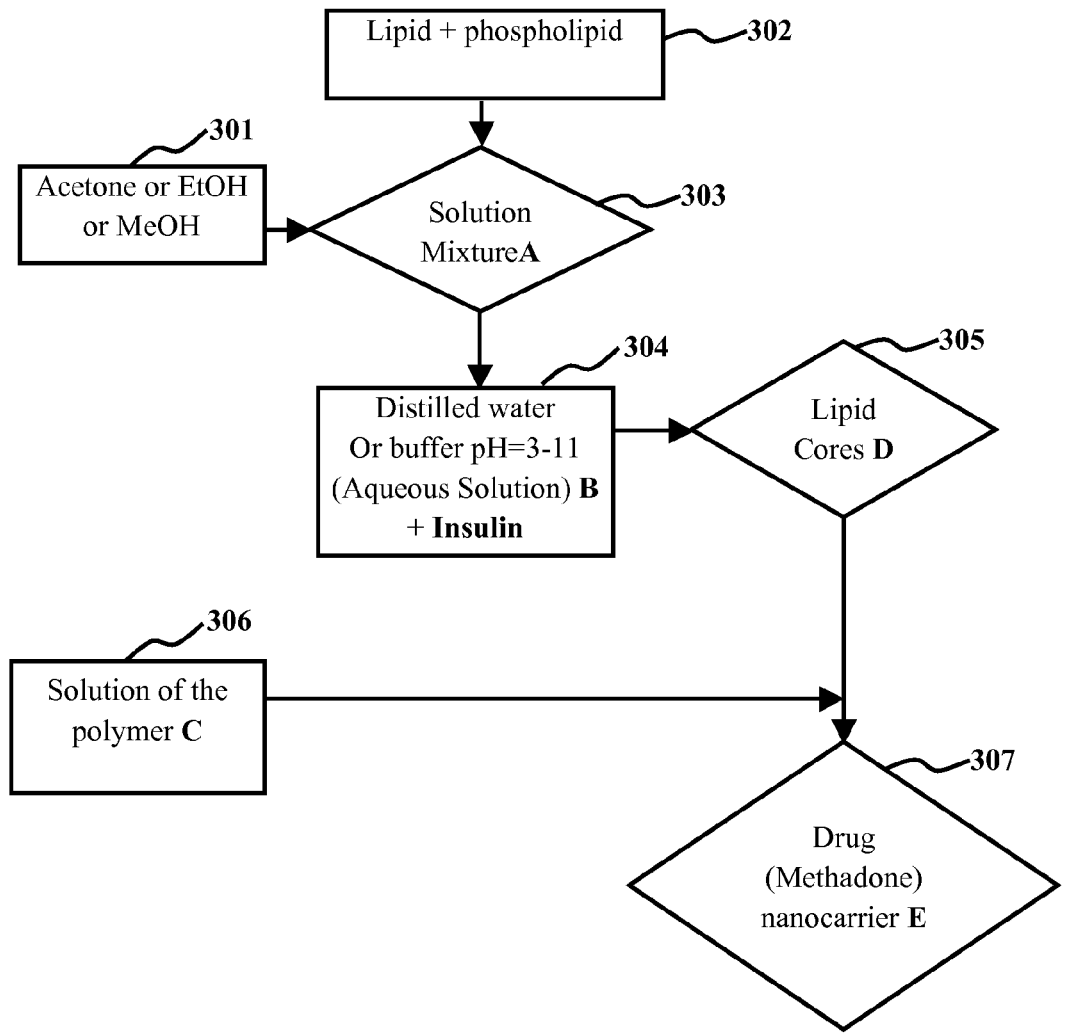
FIG. 3 illustrates a flowchart indicating a method for synthesizing a nano carrier based long acting drug delivery system for insulin, according to an embodiment herein.

FIG. 3 illustrates a flowchart indicating a method for synthesizing a nano carrier based long acting drug delivery system for insulin, according to an embodiment herein. The lipid and phospholipid are dissolved in the organic solvent. Initially the organic solvent is prepared (301). The organic solvent is selected from a group consisting of ethanol, methanol or acetone. The organic solvent has a concentration of 0.1 to 5 mg/ml. Then different amounts of the phospholipid, mainly phosphatidylcholine, are dissolved in this solution and, finally, the lipid, mainly a glyceryl stearate, is dissolved in the same solution with a preset concentration depending on the drug and the organic solvent components (302). The mixing of organic solvent with lipid and phospholipid yields a solution mixture-A (303). The insulin at different concentrations is taken based on the specific objectives, therapeutic dosages and indications. The insulin to be entrapped is taken in the concentration of 0.1 to 10 mg/ml. The insulin is dissolved in the water or a buffer (304). The solution-A is added dropwise onto an aqueous phase such as water or buffer with a pH in the range of 3-11 (304). The lipid cores-D are formed aqueous phase (305). The volume ratio of the organic to the aqueous phase mixtures is 0.05 to 3. Finally, a buffered aqueous solution of the polymer C such as a poly cation with a pH of 3.5 to 11 with different concentrations, based on the amount of other compounds, is added dropwise or in drops onto the lipid cores to form the coats around the lipid cores (306). The polymer solution is added dropwise to the organic to aqueous phase in a volume ratio of 0.05 to 1. The drug nanocarriers E comprising insulin are obtained (307). The insulin is water soluble and presents itself in the aqueous solution.

EXAMPLE 1

Synthesis of Insulin Carrying Nanoparticle/Nanocarrier

The following materials are required for the synthesis of nano carrier based drug delivery system for insulin.
Materials Required:
1. Organic solvent: methanol, ethanol, acetone, isopropanol;
2. Phospholipids: Phosphatidylcholine, phosphatidylethanolamine, phosphatidylinositol;
3. Lipids: Monostearyl glycerol, Distearyl glycerol, Palmitic acid, Stearic acid
4. Polymers: chitosan, polyethylene glycol, polyvinyl alcohol.

Procedure:
In the first step based on the specific objectives, therapeutic dosages and indications the methadone at different salts in different concentrations is taken. The lipid and phospholipid is dissolved in an organic solvent, ethanol, methanol or acetone. The organic solvent has a concentration of 0.1 to 5 mg/ml. Different amounts of the phospholipid, mainly phosphatidylcholine, are dissolved in this solution and, finally, the lipid, mainly a glyceryl stearate, is dissolved in the same solution with a preset concentration depending on the drug and the organic solvent components. The mixing of organic solvent lipid and phospholipid yields a solution mixture-A. The insulin to be entrapped is taken in the concentration of 0.1 to 10 mg/ml. The insulin is dissolved in the aqueous phase such as water or buffer. The solution-A is added dropwise onto an aqueous phase such as water or buffer with a pH in the range of 3-11 and dissolved insulin. The lipid cores-D are formed in the aqueous phase. The volume ratio of the organic to the aqueous phase mixtures is 0.05 to 3. Finally, a buffered aqueous solution of the polymer C such as a poly cation with a pH of 3.5 to 11 with different concentrations, based on the amount of other compounds, is added dropwise onto the lipid cores to form the coats around the lipid cores and the drug nanocarriers E are obtained. The polymer solution is added dropwise to the organic to aqueous phase in a volume ratio of 0.05 to 1. The insulin is water soluble and presents itself in the aqueous core.

Figure 4:
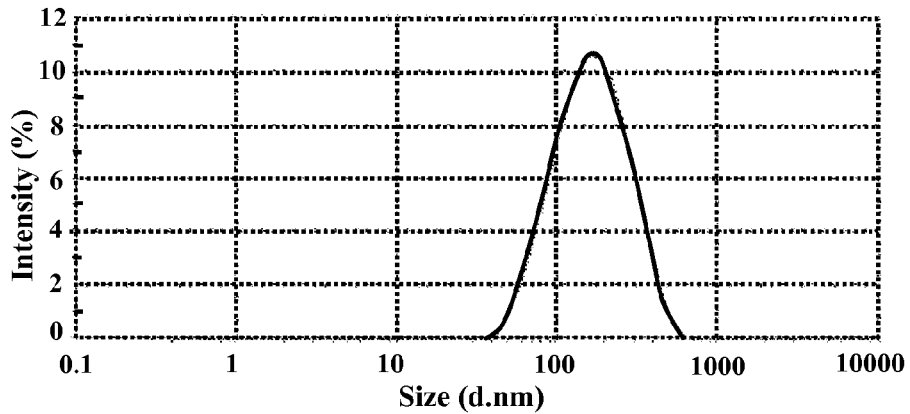
FIG. 4 illustrates a graph indicating a size distribution profile of the drug nano-carriers for insulin, according to an embodiment herein.

FIG. 4 illustrates a graph indicating a size distribution profile of the drug nano-carriers for insulin, according to an embodiment herein. With respect to FIG. 4, the particle size distribution of the nanoparticles is analyzed by DLS analysis. The curves in the graph of FIG. 4 are the long-normal probability curves. In the graph, log of the diameters of the nanoparticle populations is plotted against the relative contribution of the probability in the total number of particles based on the scattered light intensity from each sub-population. The particle size distribution curves in FIG. 4 exhibit only one peak (128.5 nm) with a relatively low polydispersity index (0.180). This indicates an ideal size of the nanoparticles with only one peak representing a unimodal size distribution.

Figure 5:
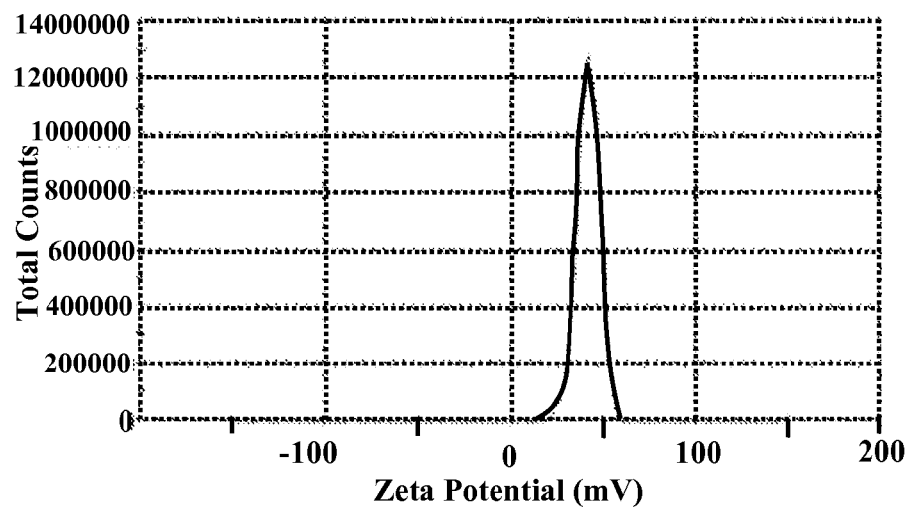
FIG. 5 illustrates a graph indicating the zeta potential distribution profile of the drug nano-carriers/nanoparticles for insulin, according to one embodiment herein.

FIG. 5 illustrates a graph indicating the zeta potential distribution profile of the drug nano-carriers/nanoparticles for insulin, according to one embodiment herein. The zeta potential characterizes the electrical potential on the surface of a colloid. This parameter is of a particular importance both regarding the in vitro stability of the nanoparticles owing to the presence of a minimum electrical repulsion between the particles and also the in vivo fate of the nanocarrier upon entry to the host organism. The fate of the nanoparticles is regarding the effect of the surface potential on the capture of the nanoparticles by the natural defence mechanisms of the organism. The zeta potential required for the stability of the nanoparticles is 10 mv-30 mv. FIG. 5 shows the in vitro stability a potential of nanoparticles to be around 30 mv is ideal but not less than 10 mv. Also for the fate of the nanoparticles, a zeta potential between +30 mv and −30 mv is ideal, but the positive potential is the mostly preferred than neutral than negative, which is shown by the nanoparticles in FIG. 5. The FIG. 5 further illustrates the narrow distribution of the zeta potentials of the nanoparticles with a zeta deviation of 4.71 mv, is a very promising result along with the unimodal distribution (only one peak) of the zeta potentials which is again promising with respect to the homogeneity of the particles.

Figure 6:
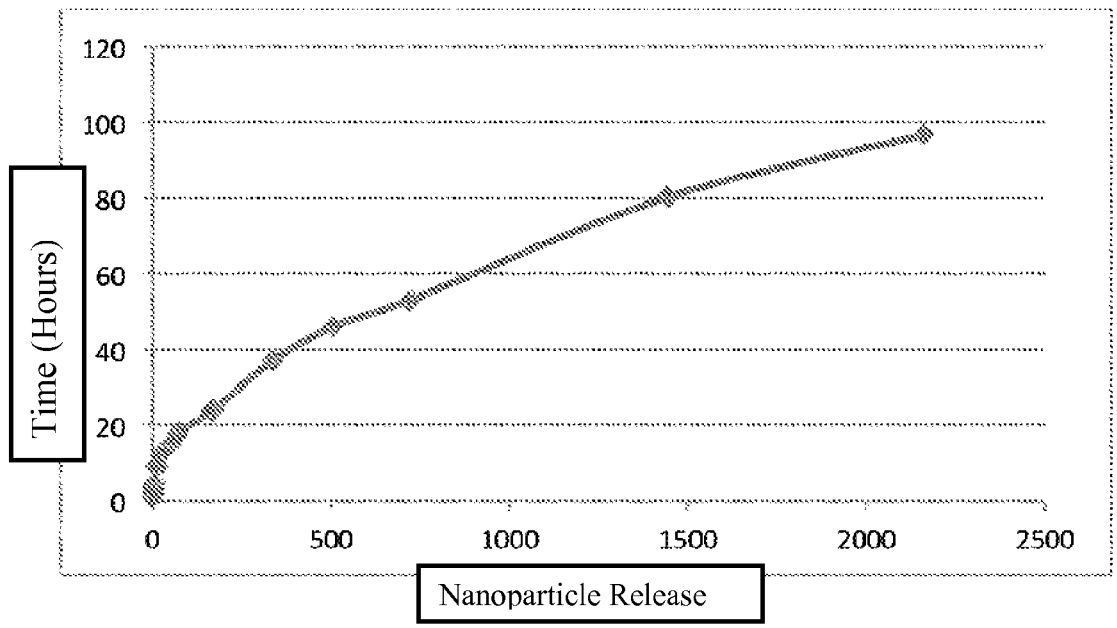
FIG. 6 illustrates a graph indicating the drug release profile of insulin from a nano carrier based long acting drug delivery system for methadone, according to one embodiment herein.

FIG. 6 illustrates a graph indicating the drug release profile of insulin from a nano carrier based long acting drug delivery system for insulin, according to one embodiment herein. In FIG. 6, the gradual release of the drug with a near-constant (a straight line) release rate is observed as an ideal behaviour of a controlled release system. FIG. 6 further illustrates the absence of a significant burst of drug release in initial stages. Also the considerable high plateau time of 36 hours is highly promising for obtaining a slow drug release system upon injection to the host body.

According to one embodiment herein, the slow release and the controlled release of the insulin is tested in vitro. A 3 ml of the nanocarrier dispersion is poured to a dialysis sac with an atomic mass of 12 KDa. The dialysis sac is placed in 50 ml phosphate buffer saline (PBS) which is stirred gently at 20 rpm at 37° C. At time 0 and the predetermined time points a 1 ml aliquot sample is removed from the external medium and is replaced with fresh PBS. The drug concentration in the aliquot sample is determined with reference to a blank free drug solution placed at the same condition. The test reveals the slow and controlled release of insulin from the nanocarrier or nanoparticle.

According to one embodiment herein, the insulin nanocarrier or nanoparticles have many advantages such that popularly available raw materials are used in the preparation of the nanocarriers. Also a cost-effective and simple method is used for the preparation of nanocarriers. The biosafety of all the ingredients used in this process is well-accepted globally, as highlighted by their approval for human use by United States Food and Drug Administration (USFDA). The average size of the nanocarriers prepared makes them, on one hand, very suitable for avoidance of the biological capture by the body defence mechanisms and, on the other hand, provides a practically reliable space for being loaded by an adequate amount of the drug. The uniformly monodispersed particles provide a reproducible matrix to be loaded by the same amounts of the drug in different batches, a feature very important for the industrial production of the nanocarriers. The narrowly distributed positive electrical potential on the nanoparticles surfaces which offers a remarkable stability both in vitro and in vivo for the nanocarriers. The constant and slow rate of the drug release from the nanoparticles, assures a long acting drug delivery system as intended by the investigators. The insulin nanocarrier does not burst release the drug from the nanocarriers.

Figure 7:
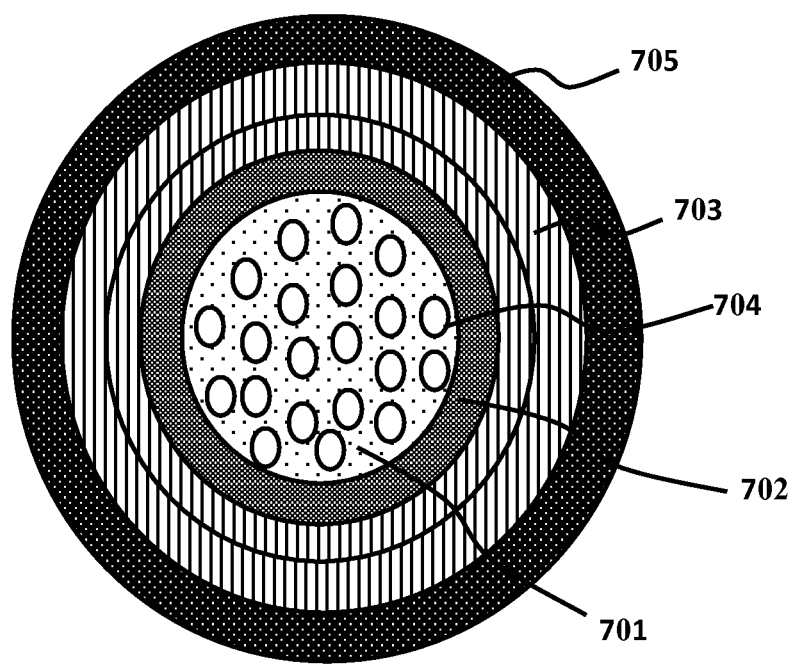
FIG. 7 illustrates a schematic structure of a nano carrier based long acting drug delivery system for insulin, according to one embodiment herein.

FIG. 7 illustrates a schematic structure of a nanocarrier based long acting drug delivery system for insulin, according to one embodiment herein. The nanocarrier drug delivery system for insulin comprises of an aqueous solution core 701. A lipid layer 702 is present around the aqueous solution. A phospholipid bilayer 703 is present around the lipid layer. The aqueous solution has the entrapped or embedded insulin drug particles 704. The outermost layer or coating of the insulin drug nanocarrier is formed by a polymer 705. The organic solvent for dissolving the lipid and phospholipid is selected from a group consisting of a methanol, an ethanol, an acetone and an isopropanol. The aqueous solution is a water or a buffer, which forms the core. The phospholipid is selected from a group consisting of a phosphatidylcholine, a phosphatidylethanolamine, a phosphatidylinositol. The lipid is selected from a group consisting of a monostearyl glycerol, a distearyl glycerol, a palmitic acid, a stearic acid and a glyceryl stearate. The polymer is selected from a group consisting of a chitosan, a polyethylene glycol, a polyvinyl alcohol.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments.

It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

Although the embodiments herein are described with various specific embodiments, it will be obvious for a person skilled in the art to practice the invention with modifications. However, all such modifications are deemed to be within the scope of the claims.

It is also to be understood that the following claims are intended to cover all of the generic and specific features of the embodiments described herein and all the statements of the scope of the embodiments which as a matter of language might be said to fall there between.

What is claimed is:

1. A composition for slow and controlled release of insulin entrapped in a nanoparticle comprising:
   an aqueous phase core with the insulin;
   a lipid selected from the group consisting of a monostearyl glycerol, a distearyl glycerol, palmitic acid, stearic acid, and glyceryl stearate;
   a phospholipid bilayer;
   and a chitosan shell or coat;
   wherein the aqueous phase core is made of water or an aqueous buffer, and wherein the insulin nanoparticle has a zeta potential between 10 mv to 30 mv, and wherein the insulin nanoparticle size distribution curve exhibits a peak of 128.5 nm, and wherein the polydispersity index of the nanoparticle population is 0.180.

2. The composition according to claim 1, wherein the phospholipid is selected from the group consisting of a phosphatidylcholine, a phosphatidylethanolamine, and a phosphatidylinositol.

3. The composition according to claim 1, further comprising a polymer selected from the group consisting of a polyethylene glycol, and polyvinyl alcohol.

4. The composition according to claim 1 which can be administered in a manner selected from the group consisting of intravenously, intramuscularly, subcutaneously, intra-dermally, intra-arterially, through the intrathecal route, and through the intra-cardiac route.

5. A method for synthesizing the composition of claim 1 comprising slow and controlled release nanoparticles in which insulin is entrapped comprising:
dissolving a phospholipid and a lipid in an organic solvent to form an organic solution, wherein the lipid is selected from the group consisting of a monostearyl glycerol, a distearyl glycerol, palmitic acid, stearic acid, and a glyceryl stearate;
dissolving an insulin in an aqueous solution with a pH in the range of 3-11, wherein the insulin is in a concentration of 0.1 mg/mL to 10 mg/mL;
adding the organic solution mixture dropwise into the aqueous solution in a volume ratio of the organic to aqueous solution of 0.05 to 3; and
adding a buffered aqueous solution of chitosan, wherein this buffered aqueous solution has a pH in the range of 3-11; wherein the polymer solution is added dropwise to the combination of the organic phase and the insulin-containing aqueous phase in a volume ratio of 0.05 to 1.

6. The method according to claim 5, wherein the organic solvent is selected from the group consisting of methanol, ethanol, acetone and isopropanol.

7. The method according to claim 5, wherein the phospholipid is selected from the group consisting of a phosphatidylcholine, a phosphatidylethanolamine, and a phosphatidylinositol.

8. The method according to claim 5, further comprising adding a polymer selected from the group consisting of a polyethylene glycol and polyvinyl alcohol.

\* \* \* \* \*